United States Patent [19]
Maruyama et al.

[11] Patent Number: 5,789,014
[45] Date of Patent: Aug. 4, 1998

[54] METHOD OF MANUFACTURING A SOLID PREPARATION COATED WITH NON-SOLVENT COATING

[75] Inventors: Naosuke Maruyama; Yuichi Nishiyama; Hiroyasu Kokubo, all of Kubiki-mura, Japan

[73] Assignee: Shin-Etsu Chemical Co., Ltd., Tokyo, Japan

[21] Appl. No.: 767,654

[22] Filed: Dec. 17, 1996

[30] Foreign Application Priority Data

Dec. 25, 1995 [JP] Japan .................... 7-350944
Jul. 19, 1996 [JP] Japan .................... 8-208920

[51] Int. Cl.$^6$ .................... B05D 1/12; B05D 1/34; B05D 3/00
[52] U.S. Cl. .................... 427/2.14; 427/2.21; 427/223; 427/214; 427/336; 427/426
[58] Field of Search .................... 427/2.16, 2.23, 427/2.19, 2.21, 2.14, 214, 212, 336, 195, 196, 202, 415, 416, 417, 426

[56] References Cited

U.S. PATENT DOCUMENTS

| | | | |
|---|---|---|---|
| 3,524,756 | 8/1970 | Signorino et al. | 427/2.19 |
| 4,533,562 | 8/1985 | Ikegami et al. | 427/2.19 |
| 4,581,381 | 4/1986 | Morris et al. | 427/2.14 |
| 4,600,645 | 7/1986 | Ghebre-Sellassie et al. | 427/2.16 |
| 4,725,441 | 2/1988 | Porter et al. | 427/2.18 |
| 4,792,450 | 12/1988 | Kydonieus et al. | 424/449 |
| 4,840,799 | 6/1989 | Appelgren et al. | 424/493 |
| 4,844,905 | 7/1989 | Ichikawa et al. | 424/451 |
| 4,894,231 | 1/1990 | Moreau et al. | 427/2.21 |
| 4,935,246 | 6/1990 | Ahrens | 424/490 |
| 4,946,685 | 8/1990 | Edgien et al. | 424/472 |
| 5,122,385 | 6/1992 | Daher et al. | 427/212 |
| 5,132,142 | 7/1992 | Jones et al. | 427/2.14 |
| 5,229,134 | 7/1993 | Mention et al. | 424/482 |
| 5,300,318 | 4/1994 | Pierre et al. | 427/212 |
| 5,470,581 | 11/1995 | Grillo et al. | 424/479 |
| 5,505,983 | 4/1996 | Kamada | 427/2.21 |
| 5,609,871 | 3/1997 | Michael et al. | 424/184.1 |

*Primary Examiner*—Diana Dudash
*Attorney, Agent, or Firm*—Townsend & Banta

[57] ABSTRACT

A method of manufacturing a solid preparation coated with a non-solvent coating which is prepared by feeding a polymeric powder directly as coating agent while continuously spraying a solid medicine with an atomized mixture of a liquid substance, which has a contact angle against the polymer coating agent of 10 degrees or less, and a plasticizer. A method of manufacturing a dry-coated solid preparation in which a solid preparation, coated with a non-solvent coating, is treated by adding or spraying an atomized water or an aqueous solution of a water soluble substance in the amount of 1–10 wt % of the solid preparation to wet said "coating layer" followed by drying.

17 Claims, No Drawings

METHOD OF MANUFACTURING A SOLID PREPARATION COATED WITH NON-SOLVENT COATING

RELATED APPLICATIONS

This application claims the priority of Japanese Patent applications No. 7-350944 filed on Dec. 25, 1995 and No. 8-208920 filed on Jul. 19, 1996, which are incorporated herein by reference.

BACKGROUND OF THE INVENTION

1. Field of the Invention

This invention relates in general to a solid preparation, and more particularly to a method of manufacturing a solid preparation prepared by coating a solid medicine with a non-solvent coating, most particularly a method of manufacturing an enteric preparation.

2. The Prior Art

A solid preparation with a coating is used for enteric properties, controlled release, moisture proofing, photolysis, masking bitter tastes, etc. For example, a solid preparation is coated to protect drugs which are sensitive to acid or to protect the stomach mucus membrane from a drug which stimulates and/or injures the stomach wall in the case of an enteric preparation, to maintain the effective concentration and the functionality of the drug in the blood in the case of a controlled release preparation, and to protect a drug which would be decomposed by moisture in the case of a moisture-proofed preparation.

For the enteric coating agent, cellulose types including cellulose acetate phthalate (CAP), cellulose acetate trimellitate (CAT), hydroxypropylmethyl cellulose phthalate (HPMCP), hydroxypropylmethyl cellulose acetate succinate (HPMCAS) and carboxymethylethyl cellulose (CMEC), vinyl types including polyvinyl alcohol acetate phthalate (PVAP) and acryl types including copolymers of methacrylic acid and ethyl acrylate are used.

For a controlled release coating agent, ethyl cellulose and acrylic acid type copolymers and waxes are used. Waxes are generally used for elution control of controlled release preparations because they are hydrophobic and do not dissolve in water.

For a coating for an enteric preparation which uses water as the solvent, Japanese examined patent publication Tokko Sho 56-12614 describes a method of dispersing a cellulose-type polymer with an average particle size of 100 micrometers or less in water which contains a gelating agent (plasticizer) with a boiling point of 100° C. Tokko Sho 57-53329 and Tokko Sho 58-55125 describes use of triacetine and triethyl citrate for the plasticizer. However, all these methods have the enteric polymer in water in which the plasticizer is dissolved and therefore there is a problem in that the temperature stability of the dispersion fluid is poor and agglomeration is caused by heating, thus rendering coating impossible. Also, the concentration of the polymer in the coating fluid has a limit because of this stability problem of the dispersion fluid and there is a problem in that coating cannot be done at high concentrations. Because of this, a large amount of energy is needed to eliminate the water used as the solvent.

For combinations of waxes and an enteric coating agent, Japanese unexamined patent publication Tokkai Sho 56-164114 discloses a method in which the enteric coating is conducted with a prior art method on granules which have been prepared by means of a wet granulation method using a composition containing a higher fatty acid or its salt with a metal, and Tokkai Sho 62-33128 proposes an enteric preparation of an interferon prepared by preparing micelles from unsaturated fatty acids and a surfactant in an aqueous system, lyophilizing it, forming it into granules and such and then conducting the enteric coating. Tokkai Sho 59-20219 proposes use of a composition containing higher fatty acids for undercoating an enteric preparation. Tokkai Sho 58-46019 proposes a method in which an enteric coating agent and an oil/fat are dissolved in a common solvent (such as ethanol and dichloroethane) and are used for the controlled release coating of a controlled release preparation of Nifedipine.

However, for all these coating methods, although they used both waxes and an enteric coating, the enteric coating itself is a prior art method using a solvent and coating and drying are time consuming.

Proposed examples of methods of coating with waxes include: Tokkai Hei 1-287019 in which a higher fatty acid, higher alcohol, higher fatty acid ester or such which has a melting point of 40° C. or higher is heated above the melting point or dissolved in an organic solvent and a coating pan or a centrifugal flow coating granulation device is used for spray coating, followed by ethyl cellulose or enteric coating; Tokkai Hei 1-287021 in which wax in a powder or pellet form with a melting point of 40°–90° C. is heated above the melting point of the wax and used for coating with a fluidized bed coating apparatus; and Tokkai Hei 2-142735 in which a lipid powder with a melting point above 40° C. was used in coating by means of mechanical stirring.

Tokkai Hei 2-292229 discloses a long-lasting preparation obtained by heating a mixture of a refractory drug, a higher fatty acid which is solid at room temperature and an enteric coating agent and kneading and granulating it when the higher fatty acid is melted. Tokkai Sho 62-181214 cites fat/oil, fatty acids and higher alcohols as low melting point substances with a melting point of 30°–100° C. and discloses a method of preparing controlled release particles in which these powder/granular low-melting-point substances are used as nuclei to which medicine is adhered by means of fusion for granulation, and the particles thus obtained, while being stirred and tumbled, are heated before talc or such is sprinkled for coating. In this method, the coating film is made tight by additionally using an enteric coating agent which is finely crushed to have a diameter of 10 micrometers or less during the talc coating process.

Tokko Sho 63-40131 describes a method in which the coating is conducted by coating with a coating polymer and a plasticizer, one after another, but it does not describe continuous coating. Also, when the amount of the plasticizer to be added is small, the product yield drops. Although the film forming properties of the film are improved by using a higher ratio of the amount of plasticizer to coating agent, there is a problem in that the degree of adhesion between the preparations also increases.

Examples of the water soluble coating agent include hydroxypropylmethyl cellulose, hydroxypropyl cellulose, methyl cellulose, Pullulan, polyvinyl alcohol and sodium carboxymethyl cellulose.

These coating agents are dissolved in an organic solvent or in water for use or are used as an aqueous latex or aqueous dispersion for coating. In all these methods, because spray coating is conducted using a coating fluid which is prepared by dissolving or dispersing a polymer coating agent into an organic solvent or water, the coating becomes impossible above a certain concentration due to the limit of the viscosity of the solution of the polymer coating agent and/or, in the case of an aqueous latex and aqueous dispersion, due to the fact that the plasticizer coexists with the coating fluid. As a result, the concentration of the polymer coating agent in the coating fluid is low, resulting in a longer process time. Therefore, development of a method which allows faster coating has been called for.

The inventors discovered that non-solvent coating which only takes a short time and does not require a drying process was possible by carrying out feeding a polymeric powder directly (sprinkle-coating using a powder polymer as a coating agent) while continuously spraying an atomized plasticizer. However, compared with a conventional coating method with a solvent, the non-solvent coating method had a problem in that the product yield was reduced because the plasticizer, atomized and sprayed onto the coating powder, did not penetrate inside due to the fact that the coating powder had acquired an aggregated form although originally it was fine powder.

Assuming the same amount of the plasticizer is used in a non-solvent coating method, compared with a conventional coating method which uses a solvent or water, the surface of the obtained coated preparation takes the form of deposited powder and a tight and perfect film layer cannot be formed, sometimes making it impossible to obtain the target coating film performance.

The reason for this is believed to be as follows. When the coating is carried out with a dry method, the film layer is formed by softening and fusing of the coating polymer caused by the plasticizer. On the other hand, when a large amount of water is used, as is the case in aqueous system coatings, in addition to softening and fusing of the coating polymer caused by the plasticizer, the drying of water shortens the intermolecular spacing between the coating polymers and helps achieve the closest packing. Therefore, it is believed that the aqueous system coatings require lesser amounts of the plasticizer to form a perfect film layer compared to dry coatings.

BRIEF SUMMARY OF THE INVENTION

The object of the present invention is to provide a coating method which forms a perfect film layer using a smaller amount of plasticizer without causing sticking of the preparation.

Based on the points made above, the inventors conducted earnest research and discovered that non-solvent coating with a high product yield which only took a short time and did not require a drying process was possible by feeding a polymeric powder directly (sprinkle-coating with a powder of polymer of coating agent) while spraying with an atomized mixture of a plasticizer and a liquid substance which had a contact angle against the polymer coating agent of 10 degrees or less, thus completing the present invention.

The inventors also conducted earnest research to solve the aforementioned problem and discovered that a perfect film layer can be formed with a small amount of plasticizer and the problem of the non-solvent coating, i.e. the coating film is not a perfect film but deposited powder, can be improved by the following method: a solid preparation, prepared by feeding a polymeric fine powder directly (sprinkle-coating a solid preparation with a fine powder coating polymer), is treated by adding or spraying an atomized water or an aqueous solution of a water soluble substance in the amount of 1-10 wt % of the solid preparation to wet said coating layer, followed by drying. The inventors discovered that this method could provide a solid preparation with a highly productive non-solvent coating which allows for a short coating time with a high product yield, thus completing the present invention.

The present invention provides a method of manufacturing a solid preparation coated with non-solvent coating which is prepared by feeding a polymeric powder directly (carrying out sprinkle-coating using a powder polymer as coating agent) while continuously spraying a solid medicine with an atomized mixture of a plasticizer and a liquid substance which has a contact angle against the polymer coating agent of 10 degrees or less.

The present invention also provides the aforementioned method of manufacturing the solid preparation wherein said liquid substance which has a contact angle against the polymeric powder (powder of polymer) of 10 degrees or less is one or more types chosen from among acetyl monoglyceride, liquid paraffin and olive oil.

The present invention also provides the aforementioned method of manufacturing solid preparation wherein the particle size of said polymeric powder (powder polymer as coating agent) is 10 micrometers or less.

The present invention also provides the aforementioned method of manufacturing solid preparation wherein said polymeric powder is hydroxypropylmethyl cellulose acetate succinate.

The present invention also provides the aforementioned method of manufacturing solid preparation wherein said plasticizer is triethyl citrate.

The present invention also provides the aforementioned method of manufacturing solid preparation wherein said solid preparation is an enteric preparation.

The present invention also provides a method of manufacturing a dry-coated solid preparation in which a solid preparation, prepared by sprinkle-coating a solid medicine with a fine powder coating polymer while spraying an atomized plasticizer, is treated by adding or spraying an atomized water or an aqueous solution of a water soluble substance in the amount of 1-10 wt % of the solid preparation to wet said coating layer, followed by drying.

The present invention also provides the method of manufacturing the dry-coated solid preparation wherein the water soluble substance is a water soluble polymer(s) and/or a water soluble saccharide(s).

The present invention also provides the aforementioned method of manufacturing the dry-coated solid preparation wherein said water soluble polymer is at least one type chosen from among hydroxypropylmethyl cellulose, methyl cellulose, hydroxypropyl cellulose, polyvinyl alcohol and Pullulan and said water soluble saccharide is sucrose.

The present invention also provides the aforementioned method of manufacturing the dry-coated solid preparation wherein said coating polymer is hydroxypropylmethyl cellulose acetate succinate.

The present invention also provides the aforementioned method of manufacturing the dry-coated solid preparation wherein said plasticizer is triethyl citrate.

DETAILED DESCRIPTION

The present invention is described in detail below.

For the liquid substance used in the present invention which has a contact angle against the polymer coating agent of 10 degrees or less, depending on the kind of the polymer coating agent, preferable are oil-like substances including acetylized monoglyceride, diethyl phthalate, polyoxyethylene sorbitan, liquid paraffin and olive oil and glycols including propylene glycol. Particularly preferable are acetyl monoglyceride, liquid paraffin and olive oil.

The wettability of the polymer coating agent is better when the contact angle is smaller, resulting in homogeneous distribution of the plasticizer in the sprinking agent and an improvement in the product yield. If this contact angle is greater than 10 degrees, then wettability is poor and highly productive coating becomes impossible.

When implementing the present invention, the contact angle can be measured using the contact angle measuring device of Kyowa Kaimenn Kagaku Ltd. The following method can be used for the measurement: dripping 50 microliters of the measurement solution on the tablets prepared at 0.5 t/P with 200 mg of powder made of the coating agent/talk=100/50.

The amount of the liquid substance in the mixture of the liquid substance and the plasticizer is preferably 10–40 wt % of the plasticizer. It should preferably be 1–40 wt % of the polymer coating agent. If it is less than 10 wt % of the plasticizer, then wettability will not be improved. If it is more than 40 wt %, then there will be an adverse effect on the film forming process.

Selection of the plasticizer used for the present invention is not limited in particular as long as it lowers the softening temperature of the coating agent and improves the film forming properties. Examples include triethyl citrate and triacetin which are liquid at ordinary temperatures and not very volatile. Particularly preferable is triethyl citrate because of its superior film forming properties.

One or more types of these plasticizers can be mixed for use. The amount to be added to the solid preparation is preferably 10–80 wt %, more preferably 30–50 wt %, of the polymeric powder as coating agent.

For the polymeric powder as coating agent used in the present invention, cellulose types including cellulose acetate phthalate (CAP), cellulose acetate trimellitate (CAT), hydroxypropylmethyl cellulose phthalate (HPMCP), hydroxypropylmethyl cellulose acetate succinate (HPMCAS) and carboxymethylethyl cellulose (CMEC), vinyl types including polyvinyl alcohol acetate phthalate (PVAP) and acryl types including a copolymer of methacrylic acid and ethyl acrylate can be used.

Examples for use as a controlled release coating agent include ethyl cellulose, acrylic acid type copolymers and waxes. Examples for use as a water soluble coating agent include hydroxypropylmethyl cellulose, hydroxypropyl cellulose, methyl cellulose, Pullulan, polyvinyl alcohol, and sodium carboxymethyl cellulose.

For the polymeric powder as coating agent (powder of polymer) used in the present invention, it must be sprinkle-coated in a powder form, and it has to be fine particles for a uniform coating. Preferable is fine powder and the average particle size is preferably 10 micrometers or less.

Hydroxypropylmethyl cellulose acetate succinate is particularly preferable for the polymeric powder as coating agent used in the present invention because it has a low film forming temperature and is easily obtained in a fine powder form.

Also, two or more types of the aforementioned polymeric powder as coating agents can be mixed for use. The coating amount of the polymer coating agent is generally in the range of 10–50 wt % of the solid medicine.

In the present invention, since the polymeric powder as coating agent is sprinkle-coated, the coating can be completed in a short time even if the coating amount is increased.

Implementation of the present invention does not require significant drying power because a solvent is not used. It is preferable to have some heating and stirring capability for softening of the sprinkled powder polymer coating agent. Examples of the apparatus include a centrifugal flow coating apparatus, a pan coating apparatus and a fluidized bed coating apparatus. Of these coating apparatuses, the centrifugal flow coating apparatus with adequate stirring capability is preferable.

Coating using the polymeric powder as coating agent comprises, for example, stirring granules or parvules of the solid preparation in a centrifugal flow coating apparatus while an atomized mixture of a plasticizer and a liquid substance which has a contact angle against the polymer coating agent of 10 degrees or less is sprayed on them and simultaneously the powder coating agent is sprinkled to coat the solid preparation. This series of operations can also be conducted by dividing it into several batches with different compositions.

After the coating, the solid preparation may be further coated with a granule adhesion preventing agent which is a mixture of one or more types chosen from among metal salts of inorganic or organic acids including talc, Carplex ($SiO_2$), magnesium stearate and calcium stearate, aqueous polymers including hydroxypropylmethyl cellulose, hydroxypropyl cellulose and polyethylene glycol and waxes including carnauba wax, bees wax and paraffin.

Also, drugs and additives (colorings, pigments, etc.) which are usually approved in pharmacology may be added to the granule adhesion preventing coating.

The coating polymer can be made into a tight and perfect film layer by using after treatment method in which a solid preparation, prepared by feeding a fine powder coating polymer without any solvent (liquid), is treated by adding or spraying an atomized water or an aqueous solution of a water soluble substance in the amount of 1–10 wt % of the solid preparation to wet said coating layer, followed by drying.

The amount of water or the aqueous solution of the water soluble substance used here is 1–10 wt % of the solid preparation. If it is 1 wt % or less, then the aforementioned effect is insufficient and a perfect film layer cannot be obtained. If it is 10 wt % or more, then moisture penetrates into the preparation and causes a problem in drugs which are sensitive to moisture.

For the water soluble substance used here, one or more types from among water soluble polymers including hydroxypropylmethyl cellulose, methyl cellulose, hydroxypropyl cellulose, polyvinyl alcohol and Pullulan and water soluble saccharides including sucrose can be used. Use of the aforementioned aqueous solutions of the water soluble substances is advantageous, compared with when just water is used, in that they form a layer which prevents adhesion among the coated preparations.

The concentration of the water soluble substance in the aqueous solution depends on the substance but should preferably be 2–10 wt %. If it is 2 wt % or less then the effect of preventing adhesion among the coated preparations after the treatment is reduced. If it is 10 wt % or more then the solution viscosity becomes too high and the surface condition of the coated preparations may deteriorate.

The after treatment is conducted by adding a prescribed amount of water or an aqueous solution of a water soluble substance for wetting, followed by drying. During this wetting period, the preparation is stirred without the drying hot air flow. It is generally sufficient if this period is long enough for water to disappear from the surface of the preparation during the stirring. The drying hot air flow is then applied for drying. The temperature of the hot air may be the temperature for conventional heat-drying. Since the amount of water used here is very small, the treatment time is short and the amount of heat required for drying is also very small. The treatment time is usually about 10 minutes.

According to the present invention, non-solvent coating which only takes a short time and does not require a drying process becomes possible and the problem of non-solvent coating, a reduction of the product yield, can be solved by feeding a polymeric powder directly as coating agent while continuously spraying with an atomized mixture of a plasticizer and a liquid substance which has a contact angle against the polymer coating agent of 10 degrees or less.

Also, according to the after treatment method of the present inventionl, the coated polymer film can be made into a tight and perfect film layer.

EXAMPLES

The present invention is described in further detail below by referring to examples. The present invention is not limited to these examples.

[Experiment 1: Preparation of the Solid Medicine (Granules Containing Riboflavin)]

2000 g of nucleus granules (Non-Pareil 101 20-24# from Freund Co., Ltd.) were put into a centrifugal flow coating apparatus (CF coater CF-360 from Freund Co., Ltd.). While an atomized aqueous solution of 5% hydroxypropyl cellulose was sprayed, powder prepared by homogeneously mixing 75 g of Riboflavin and 1175 g of corn starch was sprinkled to prepare the granules. These granules contained 2 wt % Riboflavin.

[Experiment 2: Preparation of the Solid Medicine (Tablets)]

Tablets with the following composition (180 mg per tablet) were prepared using a 8 mm diameter AR mallet with 1 t/P. The tablet hardness was 10 kg, and the disintegration time measured using solution No. 1 of the pharmacopoeia Japonica (pH 1.2) was 6 minutes.

(Composition of the Tablets)
Spray dried lactose 70 parts
Corn starch 30
L-HPC (LH-11) 10
Mg-st 0.5

[Example 1]

400 g of the granules containing Riboflavin prepared in Experiment 1 were put into the centrifugal flow coating apparatus (CF coater CF-360 from Freund Co., Ltd.). Coating was conducted at an inlet temperature of 80° C., a product temperature of 45° C. and a rotation speed of 150 rpm by sprinkling, at 24 g/min. powder prepared by homogeneously mixing 60 g of hydroxypropylmethyl cellulose acetate succinate (HPMCAS, average particle size 5 micrometers: AS-MF from Shin-Etsu Chemical Co., Ltd.) and 30 g of talc, while spraying 20 g of a mixture of triethyl citrate/acetyl monoglyceride with a mixing ratio of 3/2 at a spraying rate of 11.2 g/min. The product yield was 98%. The dissolution ratio of Riboflavin after 2 hours in solution No. 1 of pharmacopoeia Japonica (pH 1.2) was 0.1%, indicating superior acid resistance.

[Example 2]

The coating was carried out in the same manner as in Example 1 except for the fact that a mixture of triethyl citrate/liquid paraffin with a mixing ratio of 3/2 was used. The product yield was 97%. The elution ratio of Riboflavin after 2 hours in solution No. 1 of pharmacopoeia Japonica (pH 1.2) was 0.8%, indicating superior acid resistance.

[Example 3]

400 g of the tablets prepared in Experiment 2 were put into the centrifugal flow coating apparatus (CF coater CF-360 from Freund Co., Ltd.). Coating was conducted at an inlet temperature of 80° C., a product temperature of 45° C. and a rotation speed of 150 rpm by sprinkling, at 24 g/min. powder prepared by homogeneously mixing 40 g of hydroxypropylmethyl cellulose acetate succinate (HPMCAS, average particle size 5 micrometers: AS-MF from Shin-Etsu Chemical Co., Ltd.) and 20 g of talc, while spraying 20 g of a mixture of triethyl citrate/acetylized monoglyceride with a mixing ratio of 5/2 at a spraying rate of 11.2 g/min. The product yield was 95%. The pin hole test was conducted after 2 hours using solution No. 1 of pharmacopoeia Japonica (pH 1.2) with a food color added to it. As a result, no change was observed, indicating superior acid resistance.

[Comparative Example 1]

400 g of the granules containing Riboflavin prepared in Experiment 1 were put into the centrifugal flow coating apparatus (CF coater CF-360 from Freund Co., Ltd.). Coating was conducted at an inlet temperature of 80° C., a product temperature of 45° C. and a rotation speed of 150 rpm by sprinkling, at 24 g/min. powder prepared by homogeneously mixing 60 g of hydroxypropylmethyl cellulose acetate succinate (HPMCAS, average particle size 5 micrometers: AS-MF from Shin-Etsu Chemical Co., Ltd.) and 30 g of talc, while spraying 21.4 g of triethyl citrate at a spraying rate of 5.7 g/min. The product yield was 74%. Conspicuous dusting was observed during the coating process.

[Comparative Example 2]

400 g of the granules containing Riboflavin prepared in Experiment 1 were put into the centrifugal flow coating apparatus (CF coater CF-360 from Freund Co., Ltd.). Coating was conducted at an intake temperature of 80° C., a product temperature of 45° C. and a rotation speed of 150 rpm by sprinkling, at 24 g/min. powder prepared by homogeneously mixing 60 g of hydroxypropylmethyl cellulose acetate succinate (HPMCAS, average particle size 5 micrometers: AS-MF from Shin-Etsu Chemical Co., Ltd.) and 30 g of talc, while spraying 42 g of triethyl citrate at a spraying rate of 11.2 g/min. The product yield was 71%. This is because nodules were formed from the granules during the coating process (nodule ratio 24%).

Experiment 3 [The Relationship Between the Contact Angle of the Liquid Substance and the Product Yield]

The relationship between the contact angle of the liquid substance added to the plasticizer against the polymer coating agent and the product yield was evaluated.

(Measurement of the Contact Angle)
Instrument used: Contact angle meter manufactured by Kyowa Kaimenn Kagaku Ltd.
Measuring method: Powder comprising HPMCAS AS-MF from Shin-Etsu Chemical Co., Ltd./talc with a mixing ratio of 100/50 was used to prepare tablets (200 mg per tablet) with 0.5 t/P. The contact angle against these tablets was measured using the aforementioned instrument. Also, coating was carried out in the same manner as in Example 1 by using the liquid substance and the product yield is summarized in Table 1.

TABLE 1

| Liquid substance | Contact angle (degree) | Product yield (%) |
|---|---|---|
| Triethyl citrate | 12.0 | 84 |
| Acetylized monoglyceride/triethyl citrate = 2/5 | 4.6 | 98 |
| Liquid paraffin/triethyl citrate = 2/5 | 6.2 | 97 |
| Olive oil/triethyl citrate = 2/5 | 7.9 | 95 |
| Glycerine/triethyl citrate = 2/5 | 36.8 | 72 |

As shown in Table 1 above, the product yield improves when a liquid substance with a contact angle of 10 degrees or less is used.

Another method of manufacturing the solid preparation of the present invention is described below by referring to examples.

Experiment 4

2000 g of nucleus granules (Non-Pareil 101 20-24# from Freund Co., Ltd.) were put into a centrifugal flow coating apparatus (CF coater CF-360 from Freund Co., Ltd.). While an atomized aqueous solution of 5% hydroxypropyl cellulose was sprayed, powder prepared by homogeneously mixing 2000 g of pancreatin of from pharmacopoeia Japonica and 1000 g of corn starch was sprinkled to prepare the granules. These granules contained 39 wt % pancreatin. An undercoating with a solid content of 5% was applied on these granules by using hydroxypropylmethyl cellulose 2910 (product name TC-5MW from Shin-Etsu Chemical Co., Ltd.).

Experiment 5

Tablets with the following composition (180 mg per tablet) were prepared using a 8 mm diameter AR mallet with 1 t/P. The tablet hardness was 10 kg, and the disintegration time measured using solution No. 1 of the pharmacopoeia Japonica (pH 1.2) was 6 minutes. An undercoating with a solid content of 2% was applied on these tablets by using hydroxypropylmethyl cellulose 2910 (product name TC-5MW from Shin-Etsu Chemical Co., Ltd.).
Spray dried lactose 70 parts
Corn starch 30 parts
Low-substituted hydroxypropyl cellulose (Product name LH-11 from Shin-Etsu Chemical Co., Ltd.) 10 parts
Magnesium stearate 0.5 parts

[Example 4]

500 g of the granules containing pancreatin prepared in Experiment 4 were put into the centrifugal flow coating apparatus (CF coater CF-360 from Freund Co., Ltd.). Coating was conducted at an intake temperature of 80° C., a product temperature of 45° C. and a rotation speed of 150 rpm by sprinkling, at 13.0 g/min, powder prepared by homogeneously mixing 150 g of hydroxypropylmethyl cellulose acetate succinate with an average particle size of 5 micrometers (product name AS-MF from Shin-Etsu Chemical Co., Ltd.) and 45 g of talc, while spraying 70 g of a mixture of triethyl citrate/acetyl monoglyceride with a mixing ratio of 3/2 at a spraying rate of 5.0 g/min. The contact angle of acetylized monoglyceride was 4.6 degrees. The product yield was 95%, but the coating layer took the form of deposited powder. Water in the amount of 8% of the loaded granules was added, followed by 10 minutes of drying at an intake temperature of 60° C. This treatment turned the coating film into a perfect film. For these coated granules, the dissolution ratio of the drug after 2 hours in solution No. 1 of pharmacopoeia Japonica (pH 1.2) was 2.0%, indicating superior acid resistance.

[Example 5]

Coating was conducted in the same method as in Example 4 except for the fact that a 4% aqueous solution of hydroxypropylmethyl cellulose 2910 (product name TC-5R from Shin-Etsu Chemical Co., Ltd.) was prepared and added to the granules (the amount added was 8% of the granules). Similarly to Example 4, the coating film after the treatment was observed and found to be a perfect film. For these coated granules, the dissolution ratio of the drug after 2 hours in solution No. 1 of pharmacopoeia Japonica (pH 1.2) was 2.5%, indicating superior acid resistance.

[Example 6]

5 kg of the tablets prepared in Experiment 5 were put into a ventilated pan coating apparatus (Hicoater HCT-48N from Freund Co., Ltd.). Coating was conducted at an inlet temperature of 80° C., a product temperature of 45° C. and a rotation speed of 20 rpm by sprinkling, at 13 g/min, powder prepared by homogeneously mixing 400 g of hydroxypropylmethyl cellulose acetate succinate with an average particle size 5 micrometers (product name AS-MF from Shin-Etsu Chemical Co., Ltd.) and 120 g of talc, while spraying 208 g of an atomized emulsion of triethyl citrate/liquid paraffin sorbitan sesquioleate with a mixing ratio of 3/2/0.2 at a spraying rate of 5.2 g/min. The contact angle of liquid paraffin/sorbitan sesquioleate was 5.2 degrees. The product yield was 90%.

A 50% syrup was then prepared and added to the tablets (the amount added was 3% of the tablets), followed by drying for 10 minutes at 60° C. to obtain the target enteric tablets. The pin hole test was conducted on the coated tablets after 2 hours using solution No. 1 of pharmacopoeia Japonica (pH 1.2) with a water soluble dye added to it. As a result, no change was observed, indicating superior acid resistance. Also, the disintegration time of these tablets was measured using pharmacopoeia Japonica solution No. 2 (pH 6.8). The measured disintegration time was 7 minutes, indicating excellent enteric disintegration.

[Example 7]

Coating was conducted in the same method as in Example 6 except for the fact that a mixed solution of an equal amount of 25% syrup and 2% hydroxypropylmethyl cellulose 2208 (product name pharmacoat 904 from Shin-Etsu Chemical Co., Ltd.) was used instead of 50% syrup. The pin hole test was conducted on the coated tablets after 2 hours using solution No. 1 of pharmacopoeia Japonica (pH 1.2) with a water soluble dye added to it. As a result, no change was observed, indicating superior acid resistance.

[Comparative Example 3]

500 g of the granules containing pancreatin prepared in Experiment 4 were put into the centrifugal flow coating apparatus (CF coater CF-360 from Freund Co., Ltd.). Coating was conducted at an intake temperature of 80° C., a product temperature of 45° C. and a rotation speed of 150 rpm by sprinkling, at 13.0 g/min, powder prepared by homogeneously mixing 150 g of hydroxypropylmethyl cellulose acetate succinate with an average particle size of 5 micrometers (product name AS-MF from Shin-Etsu Chemical Co., Ltd.) and 45 g of talc, while spraying 75 g of a mixture of triethyl citrate/acetyl monoglyceride with a mixing ratio of 3/2 at a spraying rate of 5.0 g/min. No treatment after the coating, such as in Example 4, was conducted. The surface of the coated granules took the form of deposited powder. For these coated granules, the dissolution ratio of the drug after 2 hours in solution No. 1 of pharmacopoeia Japonica (pH 1.2) was 55.2%, indicating insufficient acid resistance.

What is claimed is:

1. A method of manufacturing a solid preparation coated with a non-solvent coating which is prepared by feeding a polymeric powder directly as coating agent while continuously spraying a solid medicine with an atomized mixture of a plasticizer and a liquid substance which has a contact angle against the polymer coating agent of 10 degrees or less.

2. The method of manufacturing the solid preparation of claim 1 wherein said liquid substance which has a contact angle against the polymeric powder of 10 degrees or less is one or more substances selected from the group consisting of acetyl monoglyceride, liquid paraffin and olive oil.

3. The method of manufacturing the solid preparation of claim 1 wherein the particle size of said polymeric powder is 10 micrometers or less.

4. The method of manufacturing the solid preparation of claim 1 wherein said polymeric powder is hydroxypropylmethyl cellulose acetate succinate.

5. The method of manufacturing the solid preparation of claim 1 wherein said plasticizer is triethyl citrate.

6. The method of manufacturing the solid preparation of claim 1 wherein said solid preparation is an enteric preparation.

7. A method of manufacturing a dry-coated solid preparation in which a solid preparation, prepared by sprinkle-coating a solid medicine with a powder coating polymer while spraying an atomized plasticizer, is treated by adding or spraying water or an aqueous solution of a water soluble substance in the amount of 1–10 wt % of the solid preparation to wet said coating layer, followed by drying.

8. The method of manufacturing the dry-coated solid preparation of claim 7 wherein the water soluble substance is a water soluble polymer(s) and/or a water soluble saccharide(s).

9. The method of manufacturing the dry-coated solid preparation of claim 8 wherein said water soluble polymer is at least one selected from the group consisting of hydroxypropylmethyl cellulose, methyl cellulose, hydroxypropyl cellulose, polyvinyl alcohol and Pullulan and said water soluble saccharide is sucrose.

10. The method of manufacturing the dry-coated solid preparation of claim 7 wherein said coating polymer is hydroxypropylmethyl cellulose acetate succinate.

11. The method of manufacturing the dry-coated solid preparation of claim 7 wherein said plasticizer is triethyl citrate.

12. A continuous manufacturing method for coating an outer surface of solid preparation particles with a non-solvent coating, comprising:

continuously applying to the outer surface of said solid preparation particles a polymeric powder coating agent while continuously and simultaneously spraying the outer surface of said solid preparation particles with an atomized mixture of a plasticizer and a liquid substance which has a contact angle against the polymer coating agent of 10 degrees or less.

13. The continuous manufacturing method for coating an outer surface of solid preparation particles with a non-solvent coating of claim 12, wherein said liquid substance which has a contact angle against the polymeric powder of 10 degrees or less is one or more substances selected from the group consisting of acetyl monoglyceride, liquid paraffin and olive oil.

14. The continuous manufacturing method for coating an outer surface of solid preparation particles with a non-solvent coating of claim 12, wherein the particle size of said polymeric powder is 10 micrometers or less.

15. The continuous manufacturing method for coating an outer surface of solid preparation particles with a non-solvent coating of claim 12, wherein said polymeric powder is hydroxypropylmethyl cellulose acetate succinate.

16. The continuous manufacturing method for coating an outer surface of solid preparation particles with a non-solvent coating of claim 12, wherein said plasticizer is triethyl citrate.

17. The continuous manufacturing method for coating an outer surface of solid preparation particles with a non-solvent coating of claim 12, wherein said solid preparation is an enteric preparation.

* * * * *